(12) United States Patent
Voss

(10) Patent No.: US 7,018,520 B2
(45) Date of Patent: Mar. 28, 2006

(54) CONCENTRATION AND CLEANUP OF NUCLEIC ACID SAMPLES

(75) Inventor: Karl O. Voss, Foster City, CA (US)

(73) Assignee: Applera Corporation, Foster City, CA (US)

(*) Notice: Subject to any disclaimer, the term of this patent is extended or adjusted under 35 U.S.C. 154(b) by 430 days.

(21) Appl. No.: 10/237,537

(22) Filed: Sep. 9, 2002

(65) Prior Publication Data

US 2003/0070925 A1    Apr. 17, 2003

Related U.S. Application Data

(60) Provisional application No. 60/318,269, filed on Sep. 7, 2001.

(51) Int. Cl.
*G01N 27/453*    (2006.01)

(52) U.S. Cl. ............... 204/604; 204/605; 204/453; 204/454

(58) Field of Classification Search ............ 204/450, 204/453, 600, 604, 454, 605; 422/100
See application file for complete search history.

(56) References Cited

U.S. PATENT DOCUMENTS

| | | | |
|---|---|---|---|
| 5,192,412 A | | 3/1993 | Kambara et al. |
| 5,552,028 A | | 9/1996 | Madabhushi et al. |
| 5,779,868 A | * | 7/1998 | Parce et al. ............... 204/604 |
| 6,013,165 A | * | 1/2000 | Wiktorowicz et al. ...... 204/456 |
| 6,017,765 A | | 1/2000 | Yamada et al. |
| 6,387,235 B1 | | 5/2002 | Irie et al. |
| 6,485,625 B1 | * | 11/2002 | Simpson et al. ............ 204/601 |

OTHER PUBLICATIONS

International Search Report from PCT/US02/28612 dated Jul. 3, 2003.
Backhouse et al., "DNA Sequencing in a Monolithic Microchannel Device," *Electrophoresis* 21:150-156 (2000), month unavailable.
Dolnik, et al., "Capillary Electrophoresis on Microchip," *Electrophoresis* 21:41-54 (2000), month unavailable.
Grossman and Colburn, "Capillary Electrophoresis Theory and Practice," Chapter 1, *Academic Press, Inc.* (1992), month unavailable.
Sanbrook et al., "Molecular Cloning: A Laboratory Manual," Second Edition, Chapter 5, Enzymes Used in Molecular Cloning, *Cold Spring Harbor Laboratory Press* (1989), month unavailable.
Woolley et al., "Ultra-high-speed DNA Fragment Separations Using Microfabricated Capillary Array Electrophoresis Chip," *Proc. Natl. Acad. Sci.* 91:11348-11352, Biophysics (1994).
Xiong, et al., "Base Stacking: pH-Mediated On-Column Sample Concentration for Capillary DNA Sequencing," *Anal. Chem.* 70: 3605-3611 (1998), month unavailable.

* cited by examiner

*Primary Examiner*—Kaj K. Olsen

(57) ABSTRACT

Methods and devices are described for concentration and cleanup of samples containing bio-molecule analytes (e.g., polynucleotides, such as DNA, RNA, PNA). Various embodiments provide for pH-mediated sample concentration and cleanup of nucleic acid samples with channel devices (e.g., cross-T format, microchannel devices).

10 Claims, 4 Drawing Sheets

CONCENTRATION AND CLEANUP OF NUCLEIC ACID SAMPLES

CROSS-REFERENCE TO RELATED APPLICATION

This application is a non-provisional of application Ser. No. 60/318,269, filed Sep. 7, 2001, which is incorporated herein by reference.

FIELD OF THE INVENTION

The present invention relates to methods and devices for the concentration and cleanup of samples containing analytes. Aspects of the invention relate to pH-mediated sample concentration and cleanup of nucleic acid samples with channel devices.

REFERENCES

Backhouse et al., DNA sequencing in a monolithic microchannel device, Electrophoresis 2000, 21, 150–156.

Dolník et al., Capillary electrophoresis on microchip, Electrophoresis 2000, 21, 41–54.

Grossman and Colburn, Capillary Electrophoresis Theory and Practice, Chapter 1, Academic Press (1992).

Kambara et al., U.S. Pat. No. 5,192,142 (1993).

Madabhushi et al., U.S. Pat. No. 5,552,028 (1996).

Sambrook et al., eds., Molecular Cloning: A Laboratory Manual, Second Edition, Chapter 5, Cold Spring Harbor Laboratory Press (1989).

Woolley et al., Ultra-high-speed DNA fragment separations using microfabricated capillary array electrophoresis chips, Proc. Natl. Acad. Sci., vol. 91, pp. 11348–11352, November 1994, Biophysics.

Xiong et al., Base Stacking: pH-Mediated On-Column Sample Concentration for Capillary DNA Sequencing. Anal. Chem. 1998, 70, 3605–3611.

BACKGROUND OF THE INVENTION

In many techniques of molecular biology, it is important to have samples of high quality. Results are generally enhanced in PCR, sequencing, fragment analysis, and so forth, when the subject bio-molecule materials are separated from potentially interfering contaminants. Thus, it is often desirable to purify/concentrate the bio-molecules (e.g., polynucleotides, such as DNA, RNA, PNA, etc.) of interest in samples prior to analysis.

In analyses utilizing laser-induced fluorescence (LIF) detection techniques, typical DNA samples often contain, in addition to dye-labeled DNA: salts, residual enzyme, DNA oligonucleotides, dNTP's, dye-labeled ddNTP's, and/or surfactants. It is generally desirable to remove all species except the subject dye-labeled DNA fragments. However, even partial purification can be useful. Thus, at a minimum, it is often desirable to remove at least some of the species that are present at higher concentration and that could interfere with the analysis.

Sample concentration can be used to improve the detection limits of various analytical methods, such as electrophoresis. For example, the starting zone length of a sample injection can be reduced by utilization of a process termed "stacking." Stacking reduces the width of the sample zone before separation, which can result in improved sensitivity and increased peak efficiency.

Xiong et al. describe a method for pH-mediated sample concentration of DNA sequencing samples on a capillary tube. While the technique of Xiong et al. might allow for sufficient signal from direct load on unpurified sequencing samples, it would not be expected to remove unincorporated dyes and contaminants that can obscure the sequencing data. Briefly, according to the method of Xiong et al., a capillary is filled with a nucleic acid DNA separation polymer. However, the polymer solution is buffered with a basic buffer that is charged at low pH but neutralized at high pH. Xiong et al. employed Tris buffer for this purpose. The first stage of the process involves a very long electrokinetic injection from unpurified sequencing reaction (e.g., right off a thermocycler with no following cleanup step). Because the sample is very salty at this point, the electrokinetic injection process is inefficient and a long injection time is needed to move enough DNA into the capillary to obtain sufficient signal. The injection time is so long that the peaks would be far too broad to achieve the necessary resolution for DNA sequencing. To re-focus the DNA starting band, Xiong et al. follow the DNA injection with a period of electrophoresis from a sodium hydroxide solution. The hydroxide migrates into the capillary, neutralizing the Tris buffer as it enters. In the area where the Tris is neutralized the conductivity becomes very low and therefore the electric field increases. The increased electric field at the injection end of the capillary allows the DNA at the back of the injection plug to travel faster than the DNA at the front of the injection plug. This refocuses the injection plug and allows for reasonable resolution to be obtained. When this technique is used with standard capillary electrophoresis, the contaminating dye labeled terminators, which are present in much higher concentration than the DNA, also migrate into the separation capillary. The large concentration of dye can migrate with the DNA and may negatively impact some section of the sequencing data.

SUMMARY OF THE INVENTION

Aspects of the present invention relate to sample concentration and cleanup; e.g., cleanup of a DNA sample to reduce or eliminate unincorporated dyes. Among other things, the present invention provides for direct loading of unpurified sequencing reactions on microfabricated separation devices. By way of the present methods and devices, the need to purify sequencing reactions (e.g., after themocycling, which typically involves centrifugation) can be reduced or eliminated.

Aspects of the present invention relate to a channel device, various embodiments of which include (i) an injection channel and a separation channel, each channel having a first end and a second end, with the separation channel intersecting the injection channel at a region between the ends of the injection channel; (ii) a first reservoir disposed for fluid communication with one of the ends of the injection channel; (iii) a first separation medium held within the injection channel; and (iv) a second separation medium held within the separation channel; wherein the second separation medium differs from the first separation medium;

Aspects of the present invention relate to a sample-manipulation method using such a channel device. For example, various embodiments of methods herein include (a) introducing a sample, including a polynucleotide-analyte component and one or more contaminants, into the injection channel; (b) introducing a pH-modulating composition into the injection channel; (c) stacking the polynucleotide-analyte component at a stacking region of the device defined by the intersection of the channels, and locating the one or more contaminants of the sample at a region between the stacking region and the second end of the injection channel; and (d) electrophoresing the polynucleotide-analyte component down at least a portion of the separation channel, with a substantial amount (e.g., a majority) of the one or more contaminants remaining in the injection channel.

Aspects of the present invention relate to a sample-manipulation method, various embodiments of which include (a) providing a channel device, the device including (i) an elongate injection channel and an elongate separation channel, each channel having a first end and a second end, with the separation channel intersecting the injection channel at a region between the ends of the injection channel (e.g., in a cross-T format), and (ii) a loading region disposed for fluid communication with the first end of the injection channel; (b) placing a sample containing a polynucleotide analyte (e.g., DNA) and one or more contaminants into the loading region; (c) applying a first driving force (e.g., electric field) sufficient to cause at least some of sample to move from the loading region into the injection channel; (d) placing a basic solution (e.g., NaOH) into the loading region; (e) applying a second driving force (e.g., electric field) sufficient (i) to cause at least some of the basic solution to move from the loading region into the injection channel, thereby causing the polynucleotide analyte to stack in the region of the intersection of the channels, and (ii) to cause at least a portion of the one or more contaminants to move to a region between the intersection of the channels and the second end of the injection channel; and (f) applying a third driving force (e.g., electric field) sufficient to cause at least a portion of the stacked DNA to move into and along at least a portion of the separation channel, leaving behind in the injection channel at least a substantial portion (e.g., most) of the contaminants.

According to various embodiments, a separation medium is placed in each of the injection and separation channels. The separation medium can be the same in each of the channels, or it can differ in one or more respects (e.g., concentration and/or composition).

Aspects of the present invention relate to a sample-manipulation method, various embodiments of which include: (a) providing a channel device, the device including an injection channel and a separation channel, each channel having a first end and a second end, with the separation channel intersecting the injection channel at a region between the ends of the injection channel (e.g., in a cross-T format); (b) introducing a sample, including a polynucleotide-analyte component (e.g., DNA) and one or more contaminants (e.g., unincorporated dye terminators), into the injection channel; (c) introducing a pH-modulating composition (e.g., a basic solution, such as NaOH) into the injection channel; (d) stacking the polynucleotide-analyte component at a stacking region of the device defined by the intersection of the channels, and locating the one or more contaminants of the sample at a region between the stacking region and the second end of the injection channel; and (e) electrophoresing the polynucleotide-analyte component down at least a portion of the separation channel, with at least a substantial portion (e.g., most) of the one or more contaminants remaining in the injection channel.

According to various embodiments, a separation medium is placed in each of the injection and the separation channels. The separation medium placed in the injection channel can differ from, or be the same as, the separation medium placed in the injection channel. In various embodiments, the separation medium in the injection channel differs from that in the separation channel in one or both of concentration and composition.

In various embodiments, the sample is a DNA sequencing sample (e.g., Sanger sequencing reaction).

Aspects of the present invention relate to a sample-manipulation method, various embodiments of which include: (a) providing a channel device, the device including (i) a first channel (e.g., an injection channel) and a second channel (e.g., a separation channel), each channel having a first end and a second end, with the second channel intersecting the first channel at a region between the ends of the first channel (e.g., in a cross-T format); (ii) a loading region (e.g., reservoir or well) disposed for fluid communication with one of the ends of the first channel; (iii) a separation medium (e.g., polymer-buffer composition) held within the first and second channels; (b) introducing a sample, including a polynucleotide-analyte component (e.g., DNA) and one or more contaminants (e.g., unincorporated dye terminators), into the channel by way of the loading region; (c) stacking the polynucleotide-analyte component at a stacking region of the device defined by the intersection of the channels, and locating the one or more contaminants of the sample at a region between the stacking region and the second end of the first channel; (d) electrophoresing the polynucleotide-analyte component down at least a portion of the second channel, with a substantial amount (e.g., at least most) of the one or more contaminants remaining in the first channel; and (e) detecting for the polynucleotide-analyte component.

Aspects of the present invention related to a channel device. According to various embodiments, the device includes: (a) an injection channel and a separation channel, each channel having a first end and a second end, with the separation channel intersecting the injection channel at a region between the ends of the injection channel; (b) a first (e.g., loading) reservoir disposed for fluid communication with one of the ends of the injection channel; (c) a first separation medium held within the injection channel; and (d) a second separation medium held within the separation channel; wherein the second separation medium differs from the first separation medium (e.g., in concentration and/or composition).

According to various embodiments, the injection and the separation channels are disposed in a cross-T format.

According to various embodiments, the device further includes a second reservoir disposed for fluid communication with the other of the ends of the injection channel.

According to various embodiments, the device further includes third and fourth reservoirs, each being disposed for fluid communication with a respective one of the first and second ends of the separation channel.

According to various embodiments, each of the first and second separation media includes a polymer component, with the polymer component in the injection channel being present at a higher concentration than the polymer component in the separation channel.

According to various embodiments, the device further includes each of the first and second separation media includes a buffer component. According to various embodiments, the buffer components differ from one another. The buffer component of the first separation medium can comprise, for example, a Tris-HCl buffer. The buffer component of the second separation medium can comprise, for example, a TAPS/Tris buffer.

According to various embodiments, one of the ends of the separation channel intersects (for fluid communication with) the injection channel.

According to various embodiments, a region between the ends of the separation channel intersects the injection channel.

BRIEF DESCRIPTION OF THE DRAWINGS

The structure and manner of operation of the invention may further be understood by reference to the following description taken in conjunction with the accompanying drawings, in which identical reference numerals identify identical or similar elements, and in which.

DESCRIPTION OF THE INVENTION

Figure 1:
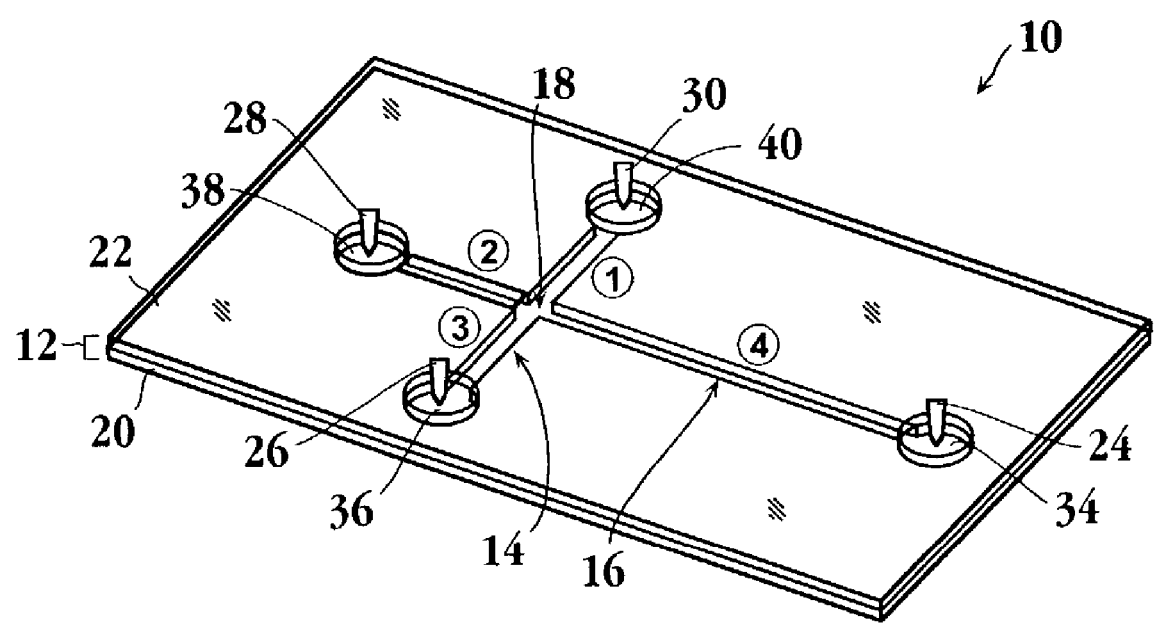
FIG. 1 is a partially schematic perspective view from one side of a microfabricated channel device, useful in practicing the present invention.

Reference will now be made to various embodiments of the invention, examples of which are illustrated in the accompanying drawings. While the invention will be described in conjunction with various preferred embodiments, it will be understood that they are not intended to limit the invention. On the contrary, the invention is intended to cover alternatives, modifications, and equivalents, which may be included within the invention as defined by the appended claims.

Unless stated otherwise, the following terms and phrases as used herein are intended to have the following meanings:

The term "channel" as used herein refers to an elongate, narrow passage or other structure (e.g., grooves, etc.) formed in a substrate and capable of supporting a volume of separation medium and/or buffer solution; e.g., such as is used in carrying out electrophoresis. The geometry of a channel may vary widely. For example, a channel can have a circular, oval, semi-circular, semi-oval, triangular, rectangular, square, or other cross-section, or a combination thereof. Channels can be fabricated by a wide range of technologies, including microfabrication techniques. As used herein, the term "channel" is not intended to encompass a capillary tube.

The terms "capillary" and "capillary tube" as used herein, refer to an elongated tubular or cylindrical structure defining an inner lumen. For example, a capillary can be an elongated capillary or micro-capillary tube made, for example, from fused silica, quartz, silicate-based glass, such as borosilicate glass, phosphate glass, alumina-containing glass, and the like, or other silica-like material(s). As used herein, "capillary" does not encompass a channel in a substrate such as a plate, slide, chip, wafer, or the like.

The terms "channel device" and "microchannel device" refer to a substrate, such as a plate, slide, chip, wafer, or similar structure, including one or more channels (e.g., grooves); and particularly those adapted at least in part for carrying out electrophoresis. Channel devices can take the form, for example, of microfabricated devices (e.g., a grooved, etched, or fluted plate, slide, chip, wafer, or other substrate).

The terms "concentrate," "purify," and "cleanup" refer to the removal or separation of a substance or material from an original, or starting, state or environment. For example, a material is said to be "purified" when it is present in a particular composition in a higher concentration than exists as it is found in a starting sample. For example, where a starting sample comprises a polynucleotide in a crude cell lysate, the polynucleotide can be said not to be purified, but the same polynucleotide separated from some or all of the coexisting materials in the cell lysate is purified. In another example, where a starting sample comprises analyte DNA and one or more contaminants, such as unincorporated dyes, salts, residual enzyme, undesired DNA oligonucleotides, dNTP's, dye-labeled ddNTP's, and/or surfactants, the analyte DNA can be said not to be "cleaned up," but the same analyte DNA separated from some or all of the contaminant(s) is said to be "cleaned up."

As used herein, the terms "separation medium" and "separation matrix" refer to a medium in which an electrophoretic separation of sample components can take place. Separation media typically comprise several components, at least one of which is a charge-carrying component, or electrolyte. The charge-carrying component is usually part of a buffer system for maintaining the separation medium at a defined pH. Media for separating polynucleotides, proteins, or other biomolecules having different sizes but identical charge-frictional drag ratios in free solution, further include a sieving component. Such sieving component is typically composed of a cross-linked polymer gel, e.g., crosslinked polyacrylamide or agarose (Sambrook), or a polymer solution, e.g., a solution of polyacrylamide, hydroxyethyl cellulose, and the like (Grossman; Madabhushi).

In various embodiments, separation channels are formed in a glass or plastic substrate, such as a plate, slide, wafer, chip, or the like, by fabrication techniques known in the art, e.g., photolithographical and/or wet-chemical etching procedures, laser ablation, electroforming, microcontact printing, microstamping, micromolding, microcasting, micromachining, engraving, and/or embossing techniques, to name a few. For example, Backhouse et al., Dolník et al., and Woolley et al (each of which is incorporated herein by reference) discuss certain microfabrication techniques that the skilled artisan can employ in making the devices of the present invention. In one embodiment, the separation channels are formed in a generally planar substrate comprised at least in part, for example, of an electrically insulating material, e.g., fused silica, quartz, silicate-based glass, such as borosilicate glass, phosphate glass, alumina-containing glass, and the like, or other silica-like material(s).

According to various embodiments of the present invention, a pH mediated stacking process is used in the injection arm of a cross-T injection arrangement, such as can be formed in a microfabricated electrophoresis device. Contaminants, such as contaminating dye terminators, migrate out into a waste region or reservoir and, thus, are not injected into an associated separation arm with the bio-molecule analyte(s).

A microfabricated device can be particularly advantageous because different polymers and/or buffers may be utilized in the injection arm and the separation channel. For example, one polymer or polymer-buffer combination can be held in the injection channel, while another (different) polymer or polymer-buffer combination can be held in the separation channel. According to various embodiments, high concentration polymer and a buffer, such as Tris-HCl [Tris (hydroxymethyl) aminomethane hydrochloride], is held in the injection arm of a channel device, while low concentration polymer and a buffer, such as TAPS/Tris [3-((2-hydroxy-1,1-bis-(-hydroxymethyl)ethyl))-amino]-1-propanesulfonic acid/[Tris(hydroxymethyl) aminomethane], is held in the separation channel.

According to various embodiments, both an injection channel and a separation channel of a cross-T channel device hold identical polymers and/or buffers. As indicated above, according to other embodiments, one or both of the buffer and polymer differ in the separation channel and the injection channel.

In certain embodiments, the buffer and/or polymer is of a higher concentration in one of the channels as compared to that held in the other of the channels. For example, a high concentration buffer can be held in one channel (e.g., about 100 mM or higher) and a low concentration buffer (e.g., 25 mM and below) can be held in the other channel. In an embodiment, the injection channel holds a high concentration buffer while the separation channel holds a low concentration buffer. In various embodiments, a high concentration polymer can be held in one channel (e.g., 5% polyacrylamide or PDMA [poly(dimethylacrylamide)], or higher) and a low concentration polymer (e.g., less than 5% polyacrylamide or PDMA) can be held in the other channel.

FIG. 1 depicts general features of one type of device in which the present invention can be embodied. It will be appreciated that other configurations may be employed. The channel device of FIG. 1, indicated generally by the reference numeral 10, comprises a substrate 12 in which channels, such as 14 and 16, are defined so as to intersect at right angles at a junction, denoted at 18. More particularly, substrate 12 is comprised of lower and upper plates, 20 and 22 respectively, with abutted confronting faces. Lower plate 20 is provided with elongate grooves, each of roughly semi-circular or semi-oval cross-section, that in part define boundaries for channels 14, 16. The lower face of plate 22 is substantially planar, and, when disposed against plate 20 as shown, further defines boundaries for channels 14, 16. Particularly, in the illustrated arrangement, the grooves of plate 20 define lower (floor) and side walls or boundaries of each channel 14, 16 and the lower surface of plate 22 provides an upper wall or ceiling (boundary) for channels 14, 16.

In various embodiments, discussed further herein, channel 14 can be employed as an "injection channel" and channel 16 can be employed as a "separation channel."

Several electrodes are provided, schematically indicated as 24, 26, 28 and 30; each being disposed for electrical communication with a reservoir, such as 34, 36, 38 and 40, respectively. One or more power sources (not shown) are disposed for electrical communication with the electrodes, permitting selective establishment of defined DC fields along the channels. For example, one DC field may be established along the injection channel. Another DC field may be established along the separation channel. The fields can be established one at a time, or simultaneously, as desired.

Reservoirs 34, 26, 38, 40 are defined by small throughholes; drilled, etched, punched, or otherwise formed through upper plate 22. Each of reservoirs 34, 36, 38, 40 is disposed for fluid communication with a respective end of one of channels 16, 18, as shown.

For reasons that will become apparent, it is convenient to refer to channels 14, 16 as comprising four segments or arms, denoted as 1, 2, 3 and 4 in FIG. 1. More particularly, segments 1, 2, and 3 are referred to herein as "side arms," or "injection arms;" and segment 4 is referred to herein as a "separation arm" or "main arm."

The channels can be any suitable length, and any suitable profile. In one exemplary configuration, main arm 4 is 50 micrometers wide (measured at its top, from one lateral side wall to an opposing lateral side wall) and 20 micrometers deep (measured from its upper ceiling or top wall to a lowermost region of its bottom wall or floor), with a length of 8.5 centimeters. The side arms can also be any suitable geometry, including non-straight geometries, and any suitable length. In this embodiment, each of side arms 1, 2, 3 has the same cross-sectional profile (width and depth) as the long channel, and a length of 1 centimeter. One suitable channel device for use in the present invention, having such dimensions, is the Standard Microfluidic Chip (Simple Cross, MC-BF4-SC) from Micralyne Inc. (Edmonton, Alberta, Canada). Multiple cross-channel or other channel arrangements can be provided on a single chip or plate, as desired. A cross-channel configuration, such as depicted in FIG. 1, is often referred to in the art as a "T" format (the "T" representing the intersection of the channels).

It should be appreciated that the present invention is not limited to the construction depicted in FIG. 1, but rather many device configurations are possible and can be used in the context of the present invention. For example, while only one T-format cross-channel arrangement is shown in FIG. 1, any reasonable number of such arrangements can be provided on a substrate. In one embodiment, both the upper and lower plates are provided with complimentary groove configurations that are aligned with one another so that corresponding upper and lower grooves cooperate to define one or more channels. In another embodiment, a plurality of spacer strips are placed between planar, parallel, opposed surfaces of confronting plates. The spacer strips, in this embodiment, define the distance separating the opposed plate surfaces, and the region between adjacent pairs of spacers defines, at least in part, each of one or more channels. Particularly, one or both of the lateral sides of each spacer define channel side boundaries and the planar confronting plate surfaces define upper and lower boundaries.

Instead of providing grooves in a lower plate that are covered by an upper plate, such as shown in FIG. 1, a channel device can include an upper plate with grooves formed along its lower surface, which can be placed over a planar upper surface of a lower plate. Moreover, although the channel device shown in FIG. 1 is disposed with its major planar surfaces disposed in a substantially horizontal fashion, the device could instead be disposed with its major planar surfaces disposed substantially vertically, or tilted at a desired angle. These and other variations and adaptations can readily be selected and implemented by the skilled artisan.

Other features that can be included in a channel device for use herein can be found, for example, in the References hereto (each of which is incorporated herein by reference).

In practice, a separation medium can be injected (e.g., pressure-filled or vacuum aspirated) or otherwise provided in the channels of the device. Exemplary separation mediums include but are not limited to agarose and crosslinked polyacrylamide. In one embodiment, GeneScan Polymer (P/N 401885) and/or POP-6 (P/N 402844) from Applied Biosystems (Foster City, Calif.) are employed as a separation medium.

In one embodiment, a sample containing a polarizable analyte and one or more contaminants is placed in one of reservoirs, 34, 36, 38, 40; and buffer solution is placed in one or more of the other reservoirs. Loading can be effected in any suitable manner, e.g., by way of a manual or automated pipette assembly.

Various embodiments of the present invention make use of a cross-channel or T-format geometry and DC electric fields to concentrate/purify DNA away from potentially interfering species in a bulk solution. Selectively applied DC fields and a pH adjustment within the injection channel results in DNA concentration into a small volume within the microfabricated device, e.g., at the intersection of the channels. Once concentrated into a small volume and purified away from at least some, and preferably most, of the potential interferences in the bulk solution, the DNA can be moved into a separation channel or collection reservoir for analysis and/or recovery.

Various embodiments are particularly adapted to biomolecule (e.g., DNA, RNA, PNA, etc.) sequence or other analysis methods, in which each of a plurality of different fragment types is labeled with a spectrally distinctive fluorescent dye. According to certain embodiments, a laser is adapted to direct an excitation beam of coherent light at a detection zone, at a location along or a separation channel, or just beyond an outlet end of such channel, of a channel device. The excitation beam excites the dyes to emit light. In various embodiments, emitted light from sample zones passes through a collection lens, through a laser light filter, and through a focusing lens. The focused light can be incident on a detector array (e.g., CCD) capable of detecting the emissions from the detection zone of the channel. Electronic signals from the detector array can provide information about the character or sequence of the bio-molecule sample.

According to various embodiments, DNA fragments of interest are concentrated and purified away from interfering species and injected into an analyzer with little or no user intervention or manipulation. In certain of the embodiments herein, DNA concentration and purification is integral with a separation device and, thus, requires no transfer of samples from the purification device to the analyzer. One such embodiment will now be described in the context of Example 1.

It is to be noted that the following example is merely illustrative, and not limiting, of the present invention.

EXAMPLE

This non-limiting example illustrates use of the present methods and devices in sample cleanup and injection; e.g., cleanup and injection of a DNA-containing sample prior to electrophoretic analysis. As this example illustrates, the methods and devices herein can be used, for example, to inject a concentrated plug of DNA into a channel, substantially free from salts and dye terminators that are in the bulk solution.

Reference is now made to FIGS. 2A, 2B, 2C and 2D, which schematically depict the present example.

Figure 2A:
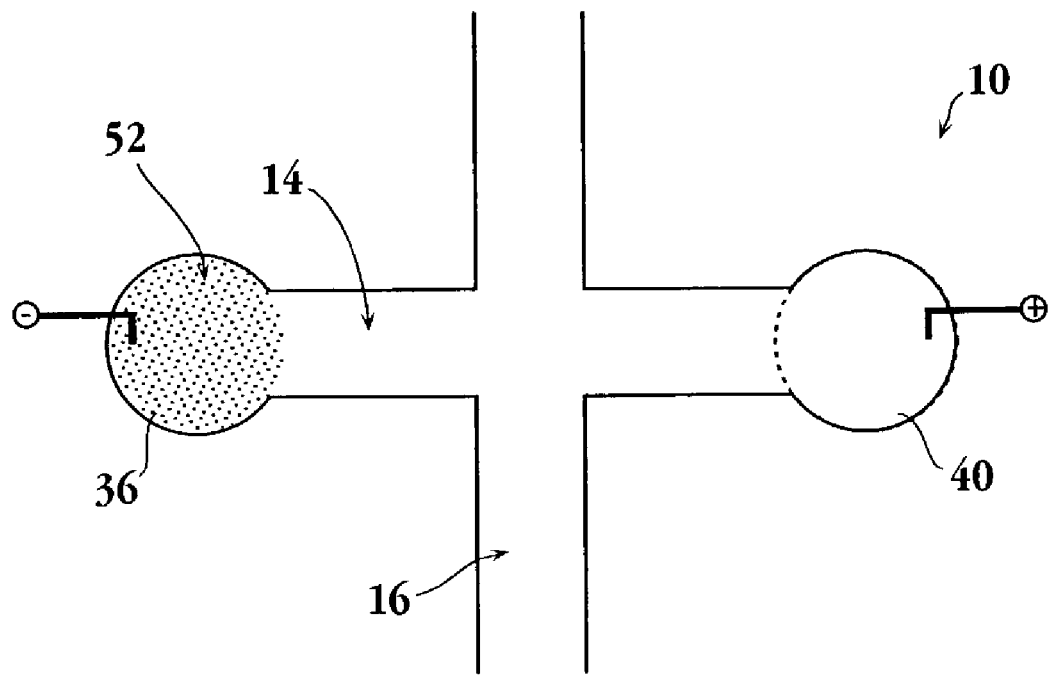
FIGS. 2A, 2B, 2C and 2D schematically depict an example of the present invention. Unpurified DNA is provided in a loading reservoir of a cross-T format channel device (FIG. 2A). The unpurified DNA sample is then caused to flow into and along an injection arm of the device (FIG. 2B). DNA is then stacked in a region whereat the injection and separation channels intersect (FIG. 2C). The concentrated DNA is then introduced into a separation arm of the device, leaving behind in the injection arm various impurities, such as unincorporated dyes (FIG. 2D).

A cross-T format channel device 10 is provided, including (i) a high concentration polymer and Tris-HCl buffer in an injection channel 14 and (ii) a low concentration sieving polymer and TAPS/Tris buffer in a separation channel 16. An unpurified DNA sample 52 is loaded in a reservoir 36 of the channel device 10 (FIG. 2A).

Figure 2B:
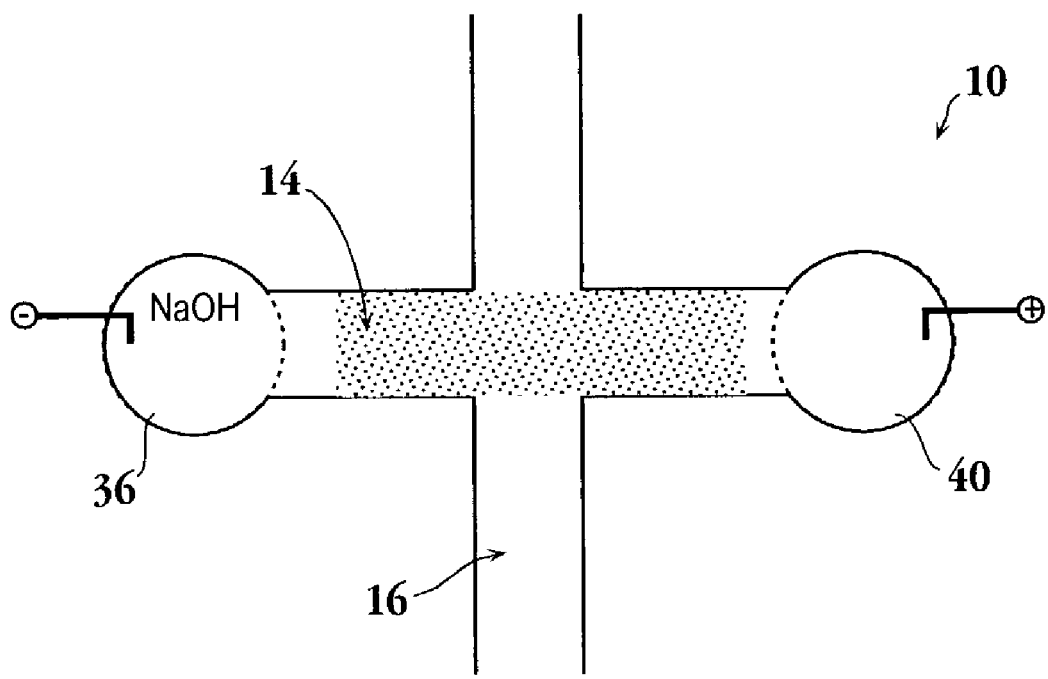

The unpurified DNA sample is then caused to flow into and along an injection arm of the device (FIG. 2B). For example, under the influence of a DC potential, the DNA-containing sample can be electrophoresed to introduce it into the device, such that DNA and potentially interfering components, such as unincorporated dyes, become distributed within injection channel 14. For example, a potential of 100V DC can be applied between reservoirs 36 and 40, thereby electrophoretically pulling DNA-containing sample into injection channel 14. Reservoir 36, which had held sample 52, is then loaded with NaOH (FIG. 2B).

Figure 2C:
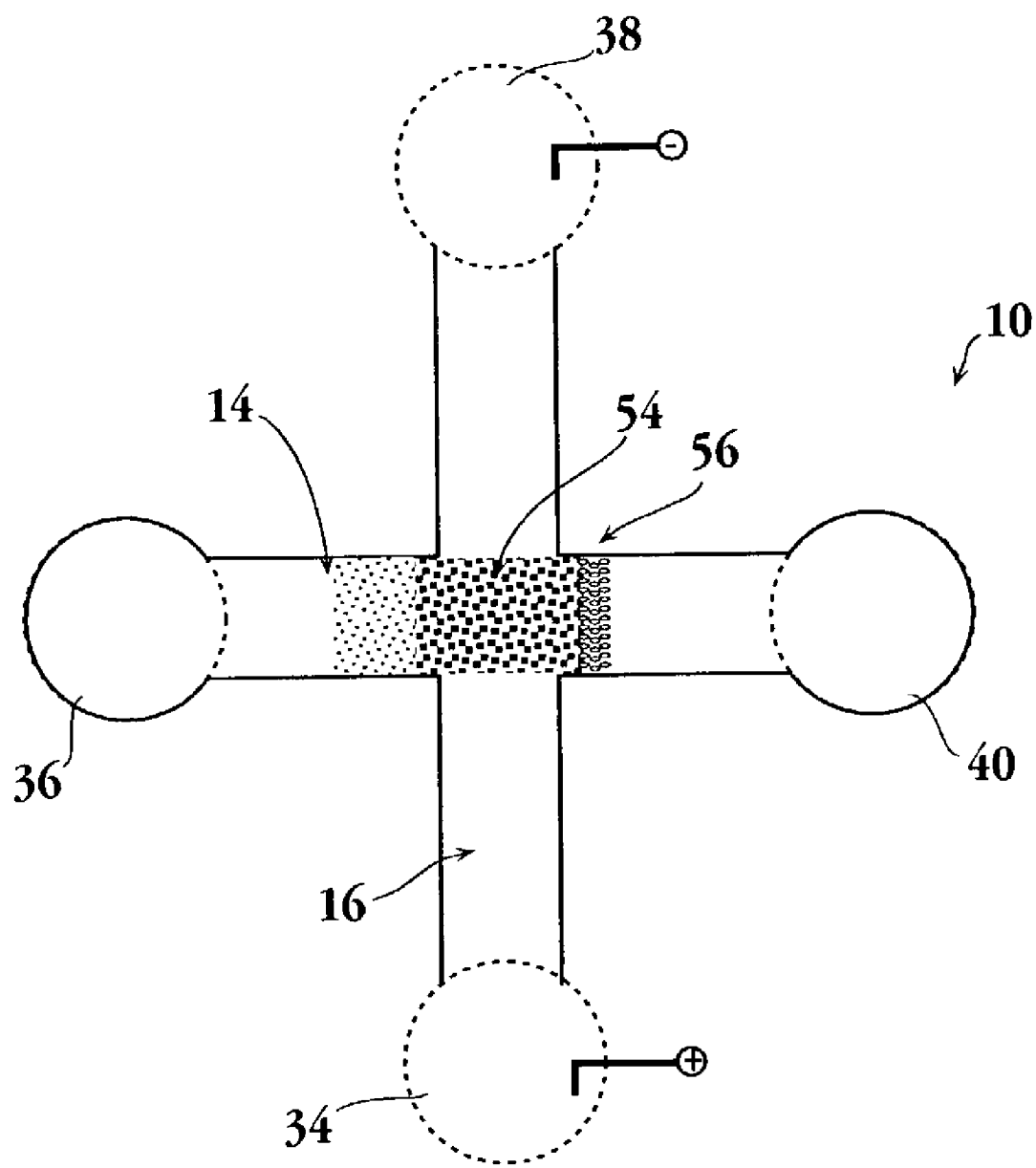

DNA is then stacked in a region whereat the injection and separation channels intersect (note the stacked DNA, indicated at 54 in FIG. 2C). This can be accomplished by electrophoresing the NaOH into injection channel 14, thereby causing the DNA to "stack up," while contaminants, such as dyes 56, migrate ahead (i.e., further downstream along the injection channel than the DNA).

Figure 2D:
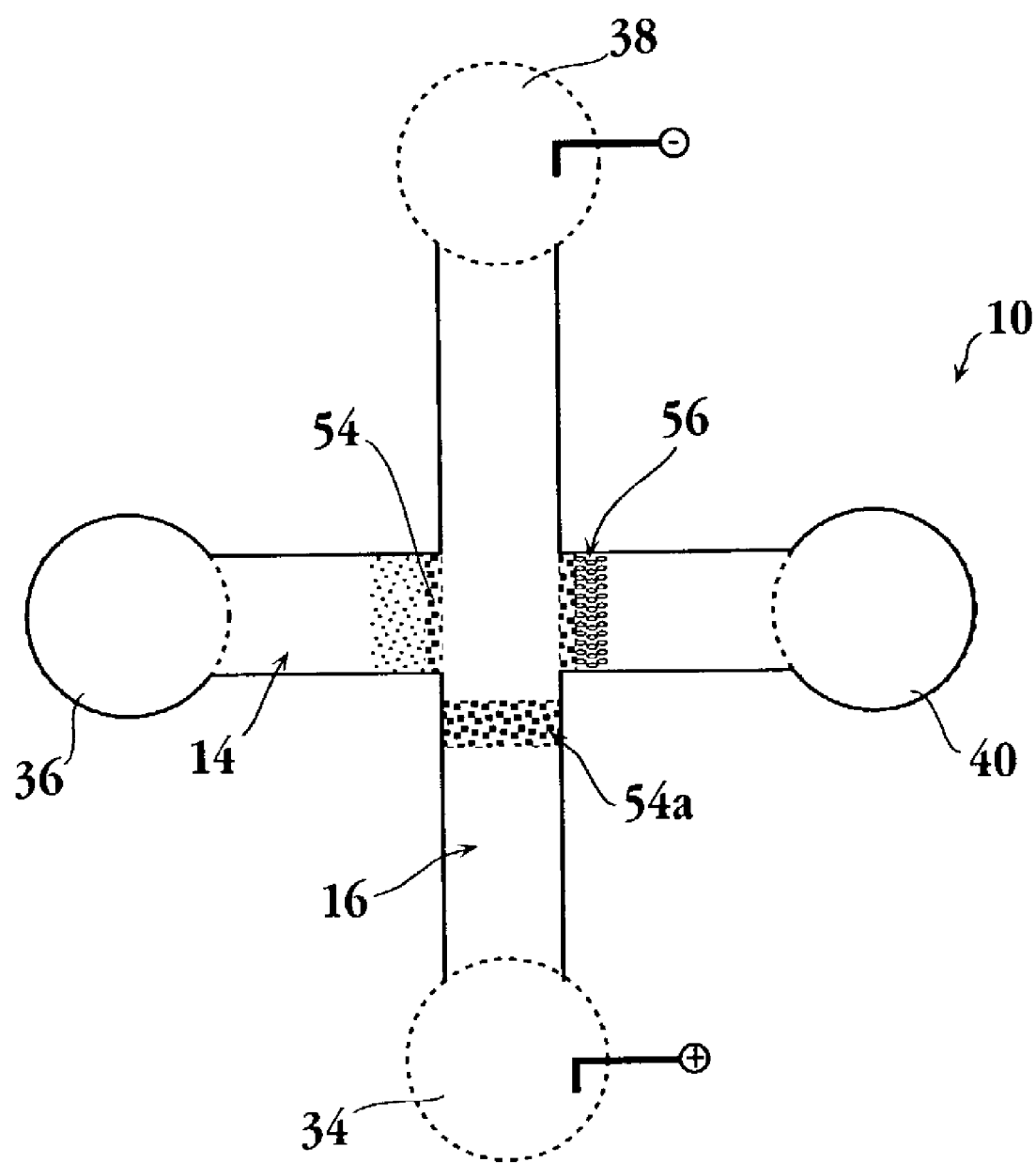

At least a portion of the stacked DNA 54 is then introduced into separation channel 16 of device 10 (FIG. 2D). For example, the DNA can be introduced into separation channel 16 by discontinuing the injection voltage along the injection channel and applying a separation voltage (1000V DC) down the length of the separation channel (see FIG. 2D). Once in the channel, the injected DNA (denoted as 54a in FIG. 2D) can be resolved. The resolved DNA can be detected (e.g., using a LIF detection arrangement disposed to observe a downstream region along the separation arm) and/or recovered.

All publications and patent applications referred to herein are hereby incorporated by reference to the same extent as if each individual publication or patent application was specifically and individually indicated to be incorporated by reference.

Those having ordinary skill in the electrophoresis art will clearly understand that many modifications are possible in the above preferred embodiments without departing from the teachings thereof. All such modifications are intended to be encompassed within the following claims.

It is claimed:

1. A channel device used to separate one or more polynucleotide analytes from one or more contaminants, the channel device comprising:
   an injection channel and a separation channel, each channel having a first end and a second end, with said separation channel intersecting the injection channel at a region between the ends of the injection channel;
   a first reservoir disposed for fluid communication with one of said ends of said injection channel; and
   a first separation medium including a first polymer component held within said injection channel and a second separation medium including a second polymer component held within said separation channel said first polymer component in said injection channel being present at a higher concentration than the second polymer component in said separation channel;
   wherein said first polymer component concentration is sufficient to separate said one or more polynucleotide analytes from said one or more contaminants on the basis of differential eletrophoretic mobilities within the injection channel such that said one or more polynucleotide analytes are purified of the one more contaminants at the intersection of the injection channel and the separation channel, and the second polymer component concentration is sufficient to separate the purified polynucleotide analytes on the basis of differential eletrophoretic mobilities within the separation channel with reduced interference from the one or more contaminants.

2. The device of claim 1, wherein said injection and separation channels are disposed in a cross-T format.

3. The device of claim 1, further comprising a second reservoir disposed for fluid communication with the other of said ends of said injection channel.

4. The device of claim 3, further comprising third and fourth reservoirs, each being disposed for fluid communication with a respective one of said first and second ends of said separation channel.

5. The device of claim 1, wherein each of said first and second separation media includes a buffer component.

6. The device of claim 5, wherein said buffer components differ from one another.

7. The device of claim 5, wherein the buffer component of said first separation medium comprises a Tris-HCl [Tris(hydroxymethyl)aminomethane]buffer.

8. The device of claim 5, wherein the buffer component of said second separation medium comprises a TAPS/Tris [3-((2-hydroxy-1,1-bis-(-hydroxymethyl)ethyl))-amino]-1-propanesulfonic acid/[Tris(hydroxymethyl)aminomethane] buffer.

9. The device of claim 1, wherein one of said ends of said separation channel intersect the injection channel.

10. The device of claim 1, wherein a region between said ends of said separation channel intersects the injection channel.

* * * * *